US010783627B2

(12) United States Patent
Madabhushi et al.

(10) Patent No.: US 10,783,627 B2
(45) Date of Patent: Sep. 22, 2020

(54) PREDICTING CANCER RECURRENCE USING LOCAL CO-OCCURRENCE OF CELL MORPHOLOGY (LOCOM)

(71) Applicant: Case Western Reserve University, Cleveland, OH (US)

(72) Inventors: Anant Madabhushi, Shaker Heights, OH (US); Cheng Lu, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 307 days.

(21) Appl. No.: 15/898,728

(22) Filed: Feb. 19, 2018

(65) Prior Publication Data

US 2018/0253841 A1    Sep. 6, 2018

Related U.S. Application Data

(60) Provisional application No. 62/466,521, filed on Mar. 3, 2017.

(51) Int. Cl.
  *G06K 9/00*      (2006.01)
  *G06T 7/00*      (2017.01)
  (Continued)

(52) U.S. Cl.
  CPC ............ *G06T 7/0012* (2013.01); *G06F 17/18* (2013.01); *G06K 9/00147* (2013.01); *G06T 7/11* (2017.01);
  (Continued)

(58) Field of Classification Search
  None
  See application file for complete search history.

(56) References Cited

U.S. PATENT DOCUMENTS 6,681,035 B1   1/2004  Bamford
8,942,441 B2   1/2015  Nielsen
(Continued)

OTHER PUBLICATIONS

Lewis Jr, James S., et al. "A quantitative histomorphometric classifier (QuHbIC) identifies aggressive versus indolent p16-positive oropharyngeal squamous cell carcinoma." The American journal of surgical pathology 38.1 (2014): 128. (Year: 2014).*

(Continued)

*Primary Examiner* — Sean M Conner
(74) *Attorney, Agent, or Firm* — Eschweiler & Potashnik, LLC

(57) ABSTRACT

Embodiments include apparatus for predicting cancer recurrence based on local co-occurrence of cell morphology (LoCoM). The apparatus includes image acquisition circuitry that identifies and segments at least one cellular nucleus represented in an image of a region of tissue demonstrating cancerous pathology; local nuclei graph (LNG) circuitry that constructs an LNG based on the at least one cellular nucleus, and computes a set of nuclear morphology features for a nucleus represented in the LNG; LoCoM circuitry that constructs a co-occurrence matrix based on the nuclear morphology features, computes a set of LoCoM features for the co-occurrence matrix, and computes a LoCoM signature for the image based on the set of LoCoM features; progression circuitry that generates a probability that the region of tissue will experience cancer progression based on the LoCoM signature, and classifies the region of tissue as a progressor or non-progressor based on the probability.

20 Claims, 8 Drawing Sheets

(51) Int. Cl.

| | |
|---|---|
| *G06T 7/45* | (2017.01) |
| *G16H 50/20* | (2018.01) |
| *G06T 7/62* | (2017.01) |
| *G06T 7/529* | (2017.01) |
| *G06F 17/18* | (2006.01) |
| *G06T 7/77* | (2017.01) |
| *G06T 7/162* | (2017.01) |
| *G06T 7/155* | (2017.01) |
| *G06T 7/11* | (2017.01) |
| *G16H 50/70* | (2018.01) |
| *G16H 50/50* | (2018.01) |
| *G16H 30/40* | (2018.01) |

(52) U.S. Cl.
CPC .............. *G06T 7/155* (2017.01); *G06T 7/162* (2017.01); *G06T 7/45* (2017.01); *G06T 7/529* (2017.01); *G06T 7/62* (2017.01); *G06T 7/77* (2017.01); *G16H 30/40* (2018.01); *G16H 50/20* (2018.01); *G16H 50/50* (2018.01); *G16H 50/70* (2018.01); *G06K 2209/05* (2013.01); *G06T 2207/10024* (2013.01); *G06T 2207/10056* (2013.01); *G06T 2207/20072* (2013.01); *G06T 2207/20076* (2013.01); *G06T 2207/30024* (2013.01); *G06T 2207/30096* (2013.01)

(56) References Cited

U.S. PATENT DOCUMENTS

| | | | | |
|---|---|---|---|---|
| 2007/0250301 | A1* | 10/2007 | Vaisberg | G01N 33/5067 |
| | | | | 703/11 |
| 2009/0297007 | A1 | 12/2009 | Cosatto | |
| 2012/0312957 | A1* | 12/2012 | Loney | G02B 21/245 |
| | | | | 250/201.3 |
| 2014/0294279 | A1 | 10/2014 | Madabhushi | |
| 2014/0315301 | A1* | 10/2014 | Hanna | A61P 15/00 |
| | | | | 435/366 |
| 2015/0254493 | A1 | 9/2015 | Madabhushi | |
| 2015/0254494 | A1 | 9/2015 | Madabhushi | |
| 2015/0254840 | A1 | 9/2015 | Madabhushi | |
| 2016/0253817 | A1 | 9/2016 | Chen | |
| 2016/0335478 | A1* | 11/2016 | Bredno | A61B 17/3423 |
| 2017/0098310 | A1 | 4/2017 | Chefd'hotel | |
| 2018/0033138 | A1 | 2/2018 | Prasanna | |
| 2018/0075279 | A1 | 3/2018 | Gertych | |
| 2018/0101949 | A1 | 4/2018 | Wang | |
| 2018/0102190 | A1* | 4/2018 | Hogue | G16H 10/60 |
| 2018/0253591 | A1 | 9/2018 | Madabhushi | |
| 2018/0253841 | A1 | 9/2018 | Madabhushi | |
| 2020/0041514 | A1* | 2/2020 | Boyden | G02B 21/16 |

OTHER PUBLICATIONS

Ali, et al. "An Integrated Region, Boundary, Shape-Based Active Contour for Multiple Object Overlap Resolution in Histological Imagery." IEEE Transactions on Medical Imaging, vol. 31, Issue 7, pp. 1448-1460. Published Jul. 2012.

Ali, et al. Graphical Processing Unit Implementation of an Integrated Shape-Based Active Contour: Application to Digital Pathology. J Pathol Inform, vol. 12, Issue 13. Published Jan. 19, 2012.

U.S. Appl. No. 15/453,500, filed Mar. 8, 2017.

Chang, Hang, Qing Yang, and Bahram Parvin. "Segmentation of heterogeneous blob objects through voting and level set formulation." Pattern recognition letters 28.13 (2007): 1781-1787. (Year: 2007).

Wahl by, Carolina, et al. "Combining intensity, edge and shape information for 20 and 3D segmentation of cell nuclei in tissue sections." Journal of microscopy 215.1 (2004): 67-76. (Year: 2004).

Parvin, Bahram, et al. "Iterative voting for inference of structural saliency and characterization of subcellular events" IEEE Transactions on Image Processing 16.3 (2007): 615-623. (Year: 2007).

Irshad, Humayun, et al. "Methods for nuclei detection, segmentation, and classification in digital histopathology: a review-current status and future potential." IEEE reviews in biomedical engineering 7 (2014): 97-114. (Year: 2014).

Notice of Allowance dated Jan. 17, 2019 in connection with U.S. Appl. No. 15/453,500.

\* cited by examiner

PREDICTING CANCER RECURRENCE USING LOCAL CO-OCCURRENCE OF CELL MORPHOLOGY (LOCOM)

CROSS REFERENCE TO RELATED APPLICATIONS

This application claims the benefit of U.S. Provisional Application 62/466,521 filed Mar. 3, 2017.

FEDERAL FUNDING NOTICE

This invention was made with government support under the National Cancer Institute of the National Institutes of Health award numbers 1U24CA199374-01, R01CA202752-01A1, R01CA208236-01A1, R21CA195152-01, R21CA179327-01A1, the National Institute of Diabetes and Digestive and Kidney Diseases under award number R01DK098503-02, National Center for Research Resources under award number 1 C06 RR12463-01, the DOD Prostate Cancer Synergistic Idea Development Award (PC120857), the DOD Lung Cancer Idea Development New Investigator Award (LC130463), the DOD Prostate Cancer Idea Development Award, and the DOD Peer Reviewed Cancer Research Program W81XWH-16-1-0329. The government has certain rights in the invention.

BACKGROUND

Computer-extracted features relating to nuclear architecture in digital pathology images may have prognostic value with respect to different cancers. By considering individual cells as nodes of a graph, edges may be constructed between vertices in a variety of ways in order to characterize the spatial arrangement of the cells and nuclei. Conventionally, graph-based prognostic approaches and systems use measurements that only consider first order statistics relating to edge lengths and node density.

One graph-based conventional approach to predicting cancer recurrence uses global graphs. Global graph-based approaches employ global graphs such as Voronoi and Delaunay triangulation strategies to connect individual cells (representing graph vertices or nodes) represented in a diagnostic image, and then compute statistics relating edge length and node density to disease outcome. Voronoi and Delaunay nuclear graphs, being fully connected graphs, describe the global spatial interactions between individual nuclei for the entire image.

Another conventional approach to predicting cancer recurrence includes using local cell cluster graphs (CCG) in which the nodes are defined on groups or clusters of nuclei rather than on individual nuclei. Similar first-order statistics, also including edge length and node density related statistics derived from the CCGs are then used to distinguish more from less aggressive disease.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
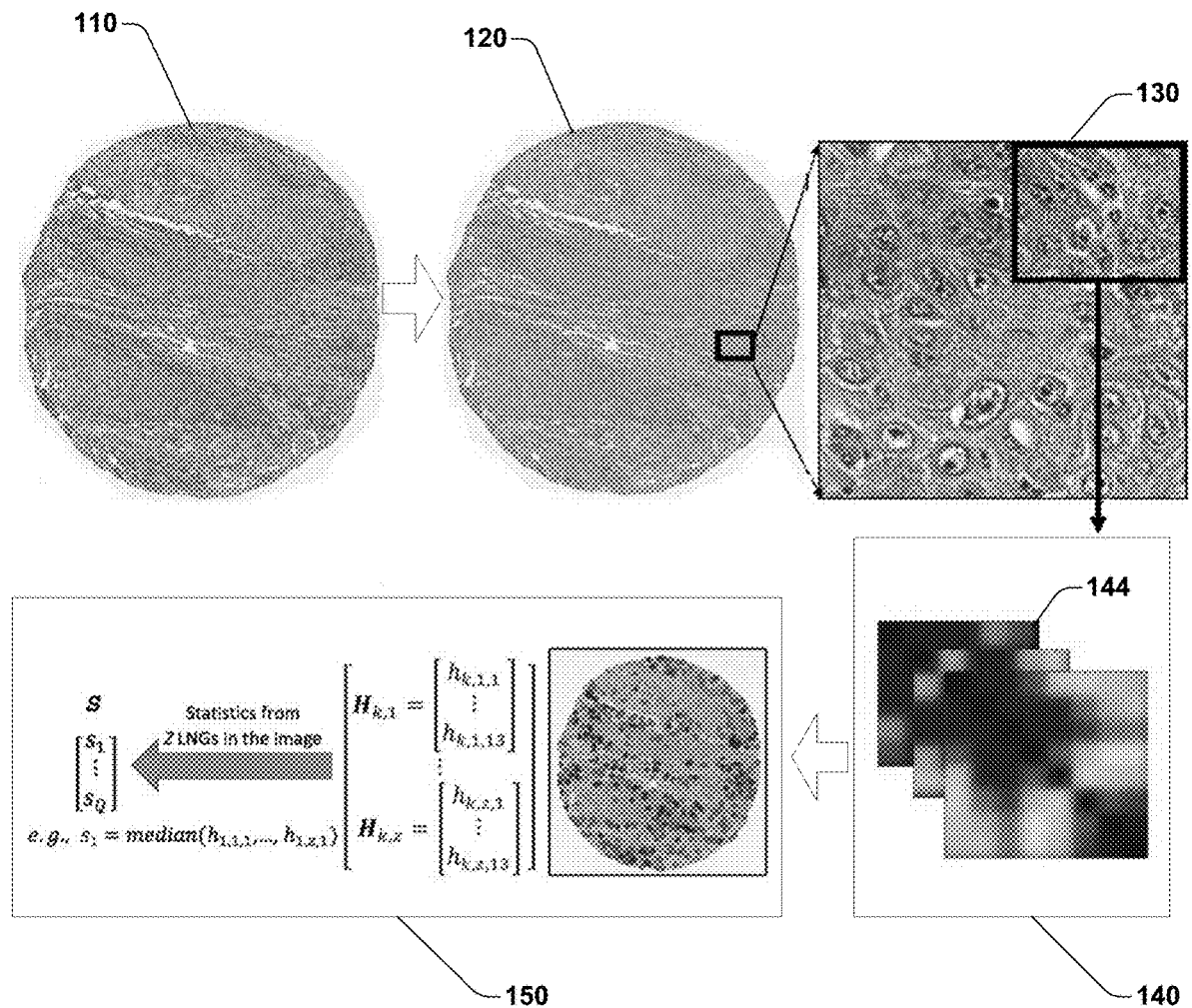
FIG. 1 illustrates an example schematic overview of a workflow to compute a local co-occurrence of cell morphology (LoCoM) signature.

Embodiments described herein predict cancer recurrence using local co-occurrence of cell morphology (LoCoM) features represented in pathology images of a region of tissue demonstrating cancer. LoCoM features are quantitative histomorphometric features that capture higher order similarity statistics between different cellular families found within a local cluster of nuclei. Embodiments using LoCoM compute co-occurrence statistics of cellular shape, size, and texture within local cell clusters to identify and characterize associations between different cellular families. LoCoM features are derived from local graph constructs, and capture intra-tumoral morphologic heterogeneity, and are then used to predict cancer recurrence using machine learning techniques.

Clinical histopathologic examination is the gold standard for diagnosing most cancers. Tumor differentiation or grade, which represents how much a tumor resembles normal squamous epithelium, has been assessed in many different ways, and is reported in routine practice. However, it holds only modest predictive value for tumor behavior in Oral cavity squamous cell carcinoma (OC-SCC), primarily early disease (Stage I or II). The growth pattern of such tumors at the leading edge may also have predictive value. Patterns of growth and host response have been shown to be prognostic, again, mostly in early stage disease.

Computational image analysis has been used to digitally mine features from digitized histologic images of tumors to predict disease aggressiveness, progression or prognosticate outcome. The identification of computer-extracted quantitative histomorphometric (QH) features that are predictive of disease behavior and outcome from routine H&E stained tissue slide images provides low cost, non-destructive companion diagnostic tools for cancer diagnosis, treatment response prediction, and prognosis. Changes in distribution, appearance, size, morphology, and arrangement of histological primitives, including nuclei and glands, can be used to predict tumor aggressiveness. For instance, in the context of prostate cancer, it is known that disease aggressiveness is characterized by differences in gland shape, morphology and arrangement. In breast cancer, tubule formation, nuclear pleomorphism, and mitotic counts comprise the Nottingham or Bloom-Richardson scoring system, which may be used in guiding clinical care decisions. In lung cancer, the texture feature on nuclear appearance and intensity distribution of the cytoplasm contain predictive and prognostic information. The shape texture features of nuclei are associated with survival in breast cancer. In some cancers, more aggressive tumor cells are prone to coordinate as a group and function as large cluster of cells.

Quantitative measurements of nuclear architecture and morphology within local cell clusters may be different between low-risk and high-risk cancers. For many different cancers, the hallmark of presence of disease is the disruption in cellular architectural cohesion between cells and primitives belonging to the same family, e.g. nuclei or lymphocytes. Conversely, aggressive tumors tend to exhibit relatively lower degrees of structure and organization between the same class of primitives. Less aggressive cancers, even though they tend to have a disruption in architecture and organization of cellular primitives, tend to have more cohesion and similarity between individual cellular primitives compared to more aggressive disease. Conventional systems and approaches to predicting cancer recurrence typically rely on first-order statistics derived from global graphs, or on first-order statistics derived from local cellular cluster graphs. Conventional systems and approaches make an assumption that all connected cells have fundamentally the same attribute and belong to the same cellular family, which is not necessarily true. These approaches do not recognize or make use of cellular diversity in local cell clusters.

Some conventional systems and approaches employ computational graph-based techniques to characterize spatial arrangement of cells and nuclei in histopathology images to predict outcome. Many of these approaches employ global graphs such as Voronoi and Delaunay triangulation strategies to connect individual cells (representing graph vertices or nodes) and then compute statistics relating edge length and node density to disease outcome. Voronoi and Delaunay nuclear graphs are fully connected graphs and thus describe the global spatial interactions between individual nuclei. However, global graph based approaches do not recognize that tumor aggressiveness might be driven more by the spatial interactions of proximally situated nuclei and cells, compared to global interactions of distally located cells. Consequently some conventional approaches employ local cell cluster graphs (CCG) in which the nodes are defined on groups/clusters of nuclei rather than on individual nuclei. Edge length and node density related statistics from the CCG are then used to distinguish more from less aggressive disease. While these CCG approaches make prognoses based on attributes relating to spatial arrangement of proximal cells, the graph connections do not discriminate between different cell populations, e.g. whether the proximal cells were all nuclei or belonged to other families such as lymphocytes. Thus, conventional approaches and systems for predicting cancer recurrence, including global graph based approaches and CCG based approaches, are sub-optimal.

Embodiments described herein employ LoCoM to capture cellular diversity based on nuclear shape, size and intensity in local cell clusters. By establishing co-occurrence statistics in terms of shape, size and texture between the nodes of a local cell cluster graph, the LoCoM feature identifies the diversity in appearance of the nodes (nuclei in this case) that constitute the graph. LoCoM employs local graph constructs to capture intra-tumoral morphologic heterogeneity, where high cellular diversity reflected in high entropy values within a cluster is reflective of high heterogeneity, and the converse for lower cellular diversity which is captured by the LoCoM feature. The LoCoM features or LoCoM signature is then used to predict recurrence or progression.

FIG. 1 illustrates a schematic workflow of one embodiment of LoCoM feature computation. A tissue micro array 110 (TMA) of a region of tissue demonstrating cancer is accessed. At 120, a multi-pass adaptive voting scheme and multi-resolution watershed are employed to identify/segment the individual nuclei. Next, at 130, a cell cluster graph algorithm is employed to create local graphs of proximally situated nuclei. Shape, size, and intensity statistics are then calculated at 140 for nodes within the local graph and co-occurrence matrices 144 based off the extracted attributives are then constructed. Second order statistics such as entropy and energy are then calculated at 150 for the co-occurrence matrices and constitute the set of LoCoM features.

Figure 2:
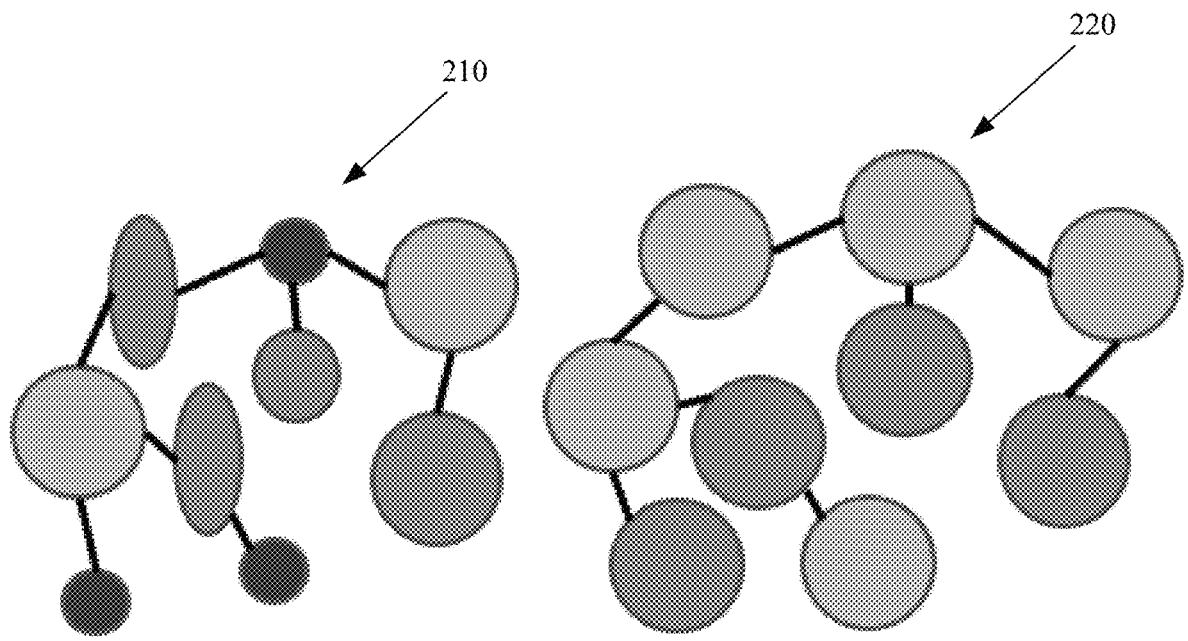
FIG. 2 illustrates example cell graphs.

FIG. 2 illustrates a cell graph 210 and a cell graph 220 that demonstrate the concept of cellular diversity. The cellular diversity of cell graph 210 is higher than that in cell graph 220 since there is substantial diversity in appearance of the nodes in cell graph 210. On the other hand, cell graph 220 shows the same graphs, but the nodes are all similar in shape and size. Even though statistics relating to edge length and node density would be identical for cell graph 210 and cell graph 220, the LoCoM features would be different.

Embodiments described herein employ LoCoM features in conjunction with a machine learning classifier to predict the risk of recurrence in OC-SCC and to predict risk of progression in p16+ oropharyngeal OP-SCC. Embodiments described herein employing LoCoM provide a comprehensive methodology to examine sub-classes of nuclei in locally packed nuclei clusters and extract and transform morphological information into feature maps and LoCoM signatures for predicting recurrence and progression. Embodiments described herein employing LoCoM quantify cellular diversity based on nuclear morphology via higher order statistical features, subsequently electronically visualizing and displaying the signature as, for example, heatmaps or other forms of feature maps. Embodiments described herein employing LoCoM generate a rich set of descriptors and use the set of descriptors to distinguish different tumor classes based on local cellular diversity with a higher accuracy than conventional approaches and conventional computerized cancer recurrence and progression prediction systems.

Example methods and apparatus demonstrably improve on conventional technologies for predicting cancer progression or recurrence. For example, embodiments described herein predict p16+ oropharyngeal OP-SCC recurrence with an average area under the receiver operating characteristic curve (AUC) of at least 0.72, compared with conventional approaches such as global cell graphs, nuclear shape, COrE, and CCG, which have lower AUC values, lower accuracy, lower specificity, and lower sensitivity. By increasing the accuracy with which cancer progression or recurrence is predicted, example methods and apparatus produce the concrete, real-world technical effect of increasing the probability that at-risk patients receive timely treatment tailored to the particular pathology they exhibit. The additional technical effect of reducing the expenditure of resources and time on patients who have a less aggressive pathology is also achieved. Example embodiments further improve on conventional approaches by providing a more accurate second reader to facilitate the reduction of inter-reader and intra-reader variability among human radiologists or oncologists. Example methods and apparatus thus improve on conventional methods in a measurable, clinically significant way. When implemented as part of a personalized medicine system or a cancer recurrence and progression prediction system, which may include a computer or a processor configured to perform methods or operations described herein, example embodiments improve the performance of a machine, computer, or computer-related technology by providing a more accurate and more reliable prediction of cancer recurrence or progression compared to conventional approaches and systems for predicting cancer progression or recurrence.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 3:
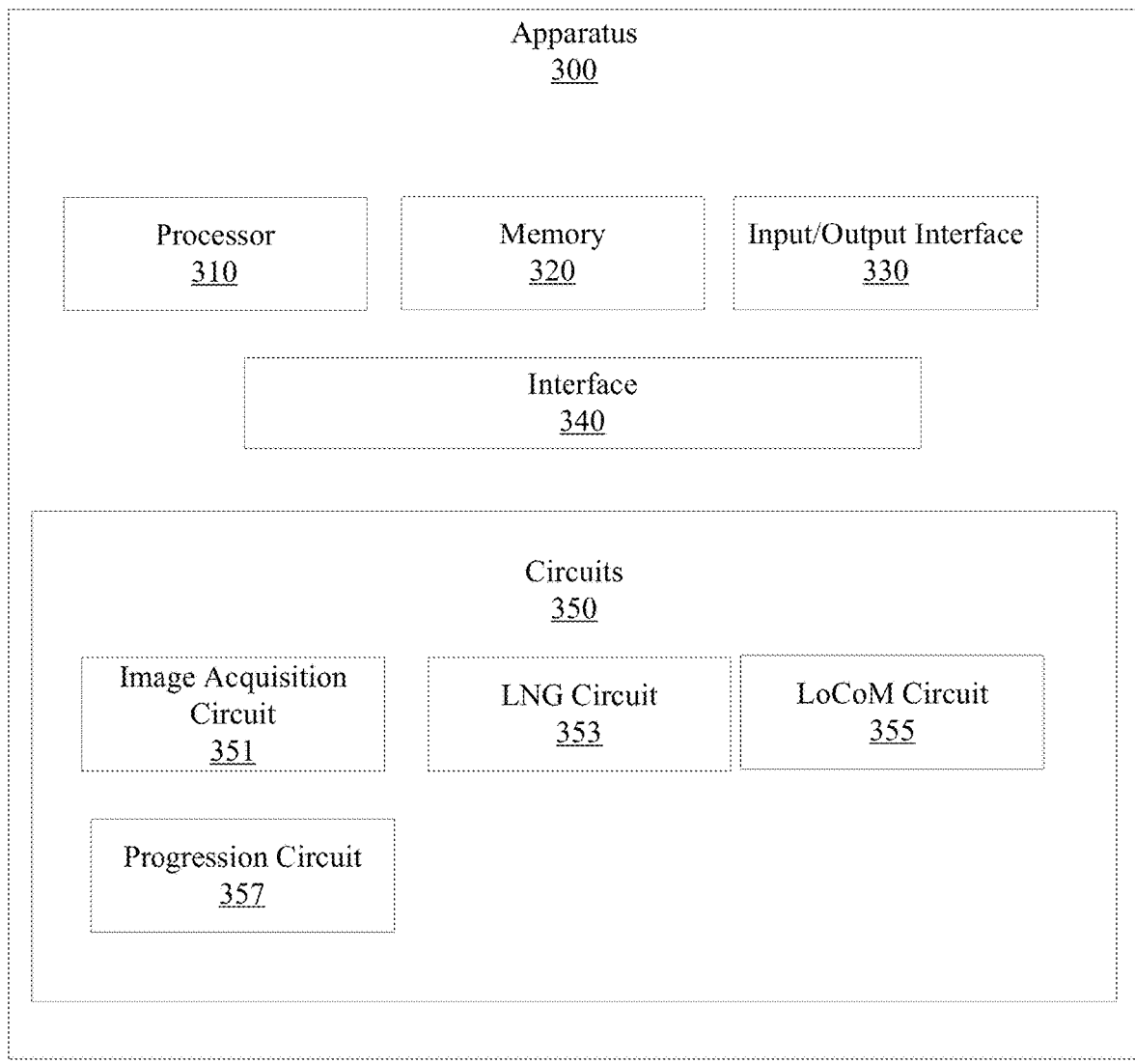
FIG. 3 illustrates an example apparatus that predicts cancer recurrence.

FIG. 3 illustrates an example apparatus 300 that predicts recurrence of cancer. Apparatus 300 includes a processor 310, a memory 320, an input/output interface 330, a set of circuits 350, and an interface 340 that connects the processor 310, the memory 320, the input/output interface 330, and the set of circuits 350. The set of circuits 350 includes an image acquisition circuit 351, a local nuclei graph (LNG) circuit 353, a local co-occurrence of cell morphology (LoCoM) circuit 355, and a progression circuit 357.

Memory 320 is configured to store a digitized image of a region of tissue demonstrating cancerous pathology. The image includes a representation of at least one cellular nucleus. The image includes a pixel, a pixel having an intensity. In other embodiments, the image may be a radiological image acquired using other imaging systems, modalities, or parameters, or be of other regions demonstrating other types of pathology.

Image acquisition circuit 351 is configured to access the image of a region of tissue demonstrating cancerous pathology. Accessing the image includes acquiring electronic data, reading from a computer file, receiving a computer file, reading from a computer memory, or other computerized activity. In one embodiment, accessing the image may include accessing a network attached storage (NAS), a cloud storage system, or other type of electronic storage system. Accessing the image may, in one embodiment, include accessing a NAS device, a cloud storage system, or other type of electronic storage system using input/output interface 330. In one embodiment, the image is an H&E stained tissue microarray (TMA) core of a region of tissue demonstrating OC-SCC or OP-SCC with a digital whole-slide scanner. In this embodiment, the TMA core is digitized at 40× magnification with a 0.25 µm per pixel resolution image. In other embodiments, other imaging approaches or parameters may be used to generate and access the image accessed by image acquisition circuit 351.

Image acquisition circuit 351 is also configured to identify at least one cellular nucleus represented in the image, where the at least one cellular nucleus has a centroid. In one embodiment, image acquisition circuit 351 is configured to identify a cellular nucleus represented in the image using multi-pass adaptive voting. In another embodiment, image acquisition circuit 351 may be configured to use other, different nuclei detection techniques, including a radial symmetry transform or a multiscale Laplacian of Gaussian filter.

Image acquisition circuit 351 is further configured to segment the at least one cellular nucleus from the background of the image. In one embodiment, image acquisition circuit 351 is configured to segment the cellular nucleus using a marker-based watershed transform. In another embodiment, image acquisition circuit 351 is configured to use other, different segmentation techniques, including an active contour model technique, region growing, and thresholding. In one embodiment, a set of n segmented nuclei is denoted as N, where $N=\{\eta_i, p \in \{1, 2, \ldots, n\}\}$.

LNG circuit 353 is configured to construct an LNG based on the at least one cellular nucleus identified by image acquisition circuit 351. A vertex in the LNG may, in one embodiment, correspond with a cellular nucleus centroid. Embodiments are configured to employ LNGs to group nuclei in local clusters to better characterize the interactions between nuclei locally and to extract nuclear properties that quantify tumor morphology more efficiently than conventional approaches and systems.

Formally, a LNG is defined as a graph $G=(N_G; E_G)$, where $N_G$ represents the vertices of the graph (which in this embodiment, represent the nuclei centroids), and $E_G$ represents the set of edges connecting the nuclei within G. Embodiments construct an LNG by linking nearby nuclei based on vicinity criteria as follows: $P(\eta_u, \eta_v)=d(\eta_u, \eta_v)^{-\alpha}$, where $\eta_u$ and $\eta_v$ are two vertices (e.g., nuclei) in the LNG, and $d(\eta_u, \eta_v)$ represents the Euclidean distance between the two vertices. Parameter $\alpha$ controls the density of the graph. $P(\eta_u, \eta_v)$ may be defined as the probability that two nuclei have a pairwise spatial relationship, i.e., that the two nuclei should be connected in an LNG. The probability of the nuclei being connected is a decaying function of the relative distance and quantifies the possibility that one of the two nuclei has grown from the other. Since this probability decreases with an increase in distance, embodiments probabilistically define an edge set E such that: $E=\{((\eta_u, \eta_v): r<d(\eta_u, \eta_v)_{-\alpha}, \forall \eta_u, \eta_v \in N$, where $r \in [0,1]$ is an empirically determined parameter. In this embodiment, r=0.2. In another embodiment, r may have another, different value. Embodiments establish the edges of an LNG using the decaying probability function with an exponent of $-\alpha$, where $\alpha \geq 0$. The value of $\alpha$ determines the density of the edges in the LNG. Thus, larger values of α generate sparser graphs. As α approaches 0, the graphs become more densely connected and approach a complete graph. In one embodiment, α may be user adjustable. In one embodiment, the value of α may be adjusted to optimize the computational efficiency of apparatus 300 or 500 or computer 800. The value of α may be adjusted as a function of computational efficiency or predictive accuracy.

LNG circuit 353 is also configured to compute a set of nuclear morphology features for a nucleus represented in the LNG. Nuclear morphology features may include a shape feature or a texture feature. Nuclear morphology features may be extracted from the LNG based on the segmented nuclei. Nuclear morphology features, including shape and texture features, quantify the morphology of a nucleus. In one embodiment, a feature extracted for a nucleus $\eta_i$ is denoted as $m_j(\eta_i)$. For a nucleus, a set of nuclear morphology features may be denoted as $M=\{m_j(\eta_i), j \in \{1, \ldots, k\}\}$. In one embodiment, seven (7) nuclear morphologic features are extracted. Thus, in this embodiment, $M=\{m_j(\eta_i), j \in \{1, \ldots, 7\}\}$. In this embodiment, the set of nuclear morphology features include an area feature that captures the size of nuclei, an eccentricity feature that captures the shape of nuclei, and an orientation feature that captures the orientation of nuclei. The set of nuclear morphology features also includes a mean intensity inside the nuclei feature that captures the intensity of nuclei appearance, and an intensity range inside the nuclei feature that captures the intensity range within nuclei appearance. The set of nuclear morphology features further includes a mean intensity outside the nuclei feature that captures the intensity range of a nuclear neighbor region, and an intensity range outside the nuclei feature that captures the intensity range around the nuclei. In another embodiment, another, different number of nuclear morphology features, or different nuclear morphology features, may be extracted.

LoCoM circuit 355 is configured to construct a co-occurrence matrix (CM) based on the set of nuclear morphology features. In one embodiment, constructing the co-occurrence matrix based on the set of nuclear morphology features includes discretizing a member of the set of nuclear morphology features along a feature dimension. Discretizing the member of the set of nuclear morphology features along the feature dimension categorizes a nucleus into a sub-class associated with the member of the set of nuclear morphology features.

Embodiments unravel the interactions between nuclei and identify higher order interactions relating to local nuclear morphology using the CM. The CM enables the capture of frequency of co-occurrence of diverse features for different nuclei within the LNG. Thus, if all the nuclei are identical in appearance, the co-occurrence matrix is a 1×1 matrix. On the other hand, the greater the diversity and range of attributes, the larger the co-occurrence matrix.

In one embodiment, the members of the set of nuclear morphology features $m_j(\eta_i)$ are discretized along each feature dimension such that $\overline{m}_j(\eta_i) = \omega*[m_j(\eta_i)/\omega]$, where ω is a quantifying factor. The discretization operation categorizes the nuclei into sub-classes in terms of a morphological feature mj. For example, if we consider the nuclear size as a morphological feature, with ω=3, we can now categorize nuclei into three sub-classes: for example, nuclei with large size, medium size, and small size. In one embodiment, ω may be selected to optimize the computational efficiency of apparatus 300 or apparatus 500, or computer 800, or may be selected as a function of computational efficiency or predictive accuracy.

In one embodiment, to construct a CM, nuclei that form nodes within a LNG are considered. In one embodiment, all the nuclei within an LNG are considered. In another embodiment, a threshold level of nuclei within an LNG are considered. Embodiments denote the LNG in a histology image as $G_k, k \in \{1, \ldots q\}$, where q is the total number of LNGs in the image. For a $G_k$ in conjunction with a particular nuclear morphologic feature, embodiments construct a c×c CM, denoted as $C_{G_k}^{m_j} \cdot C_{G_k}^{m_j}$ captures the cooccurrence frequency of nuclear sub-classes, in turn regularized by morphological feature mj, and can be expressed as follows:

$$C_{G_k}^{m_j} = \frac{1}{\sum_{a,b=1}^{\omega} C_{G_k}^{m_j}(a,b)} \begin{bmatrix} C_{G_k}^{m_j}(1,1) & C_{G_k}^{m_j}(1,2) & \ldots & C_{G_k}^{m_j}(1,\omega) \\ \vdots & \vdots & \vdots & \vdots \\ C_{G_k}^{m_j}(\omega,1) & C_{G_k}^{m_j}(\omega,2) & \ldots & C_{G_k}^{m_j}(\omega,\omega) \end{bmatrix}$$

where $$C_{G_k}^{m_j}(a,b) = \sum_{\eta_u, \eta_u}^{G_k} \begin{cases} 1, & \text{if } m_j(\eta_v) = a \text{ and } m_j(\eta_v) = b \\ 0, & \text{otherwise} \end{cases}.$$

Figure 4:
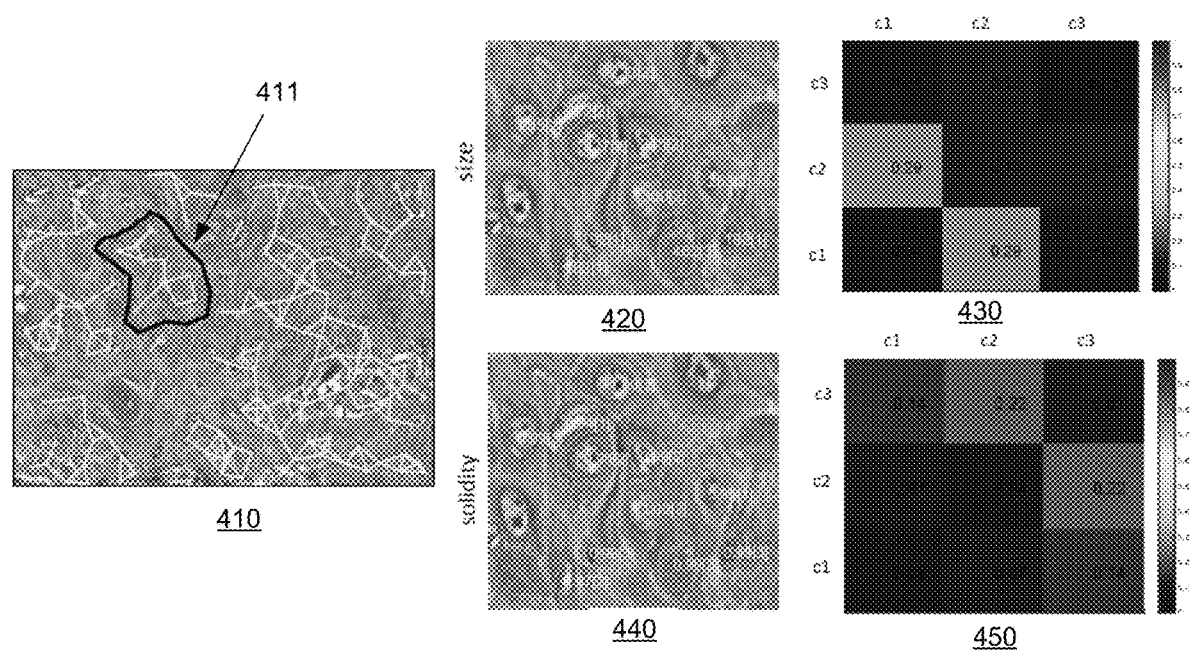
FIG. 4 illustrates an example digitized hematoxylin and eosin (H&E) stained image with overlaid local nuclei graphs (LNG) and corresponding co-occurrence matrices.

FIG. 4 illustrates an original H&E stained image 410 overlaid with LNGs. An LNG 411 is highlighted in image 410. A first magnified region 420 of image 410 depicts overlaid LNGs (α=0.45). A second magnified region 440 illustrates the same magnified region of 410 with overlaid LNGs, but at a different density (α=0.42). Co-occurrence matrices 430 and 450 illustrate nuclei captured in LNG 411 categorized into three groups, in terms of nuclear size and nuclear solidity, respectively. Note that different nuclear features result in different nuclei sub-class groups. By considering different types of nuclear features (e.g., solidity, size) different CMs may be generated (e.g., CM 430, CM 450), which demonstrate different characteristics even though they are based on the same underlying LNG 411. Thus, embodiments described herein are able to mine sub-visual information from different feature spaces represented in the same underlying imagery that conventional approaches ignore or are incapable of considering.

LoCoM circuit 355 is also configured to compute a set of LoCoM features for the co-occurrence matrix. In one embodiment, computing the set of LoCoM features includes computing a set of Haralick texture features based on the co-occurrence matrix. Computing the set of LoCoM features further includes extracting a set of second-order statistical features from the set of Haralick features.

Figure 6:
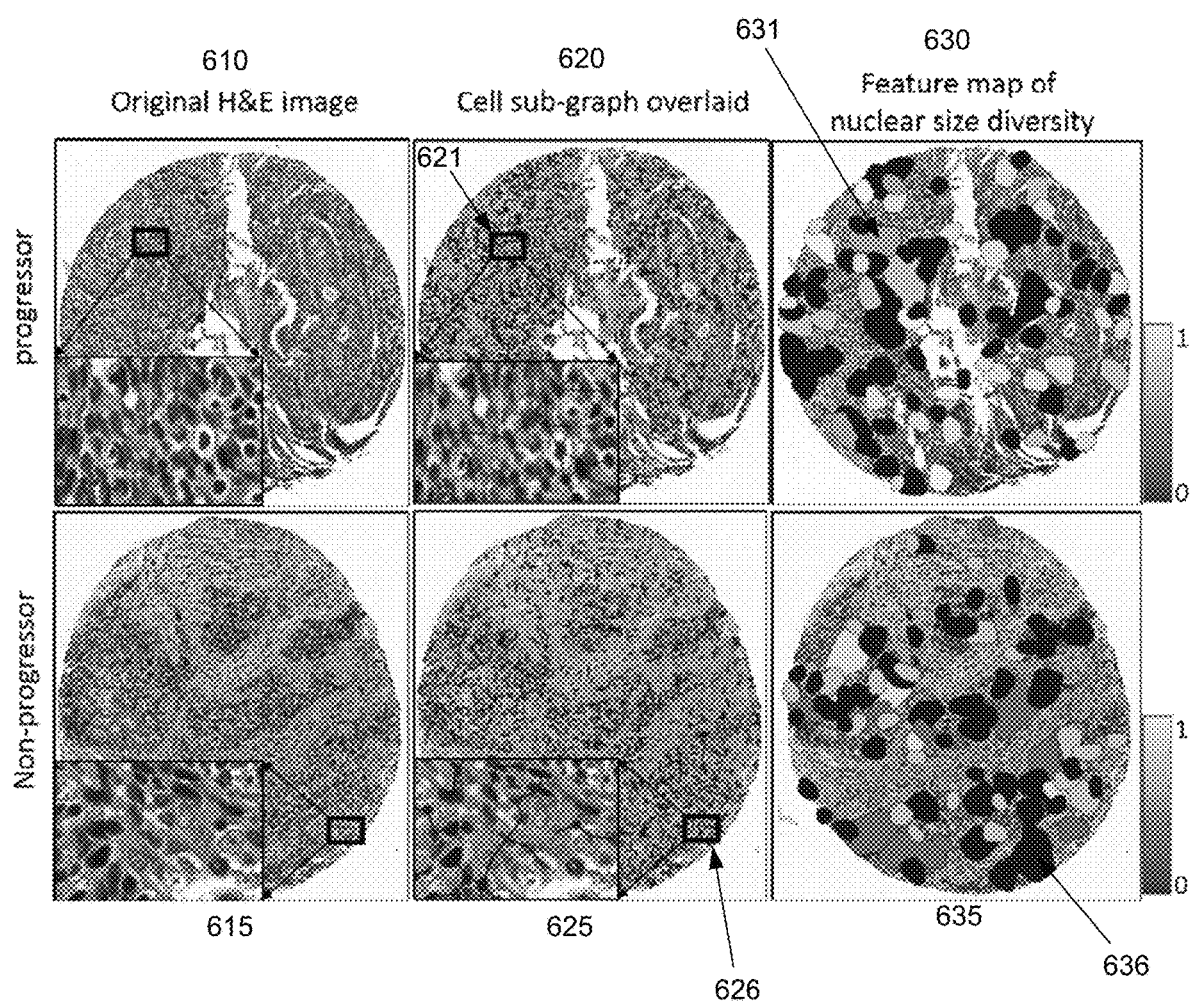
FIG. 6 illustrates exemplary LoCoM feature maps.

In one embodiment, second-order statistical features based on thirteen (13) Haralick features are extracted from a CM $C_{G_k}^{m_j}$. Higher order statistical features for an LNG $G_k$ are denoted as $H_k=[h_{k,1}, \ldots, h_{k,13}]$. In this embodiment, the feature value is displayed via a color feature map superimposed on the associated LNG, as illustrated in FIG. 6. A feature with a higher magnitude indicates a case of a high recurrence risk tumor, while a low recurrence risk tumor will have a lower feature magnitude, demonstrating the degree of disorder in terms of the morphology within the LNG. Displaying the feature map may include displaying the feature map on a computer monitor, a smartphone display, a tablet display, or other displays, or printing the feature map.

LoCoM circuit 355 is further configured to compute a LoCoM signature for the image based on the set of LoCoM features. Computing the LoCoM signature includes computing a set of first-order statistics from the set of second-order statistics. A histology image may have at least one LNG, and may have a plurality of LNGs. See, for example, H&E stained image 410 overlaid with LNGs including LNG 411. Thus, embodiments are configured to compute a set of first-order statistics that may include a mean, a standard deviation, a kurtosis, a skewness, and a range, to obtain the LoCoM signature.

In one embodiment, the mean $S_\mu$ is defined as $$S_\mu = \frac{1}{q}\sum_{k=1}^{q} H_k.$$

In one embodiment, the standard deviation $S_\sigma$ is defined as $$S_\sigma = \sqrt{\frac{1}{q}\sum_{k=1}^{q}(H_k - S_\mu)^2}.$$

In one embodiment, the kurtosis $S_K$ is defined as $$S_K = \frac{S_\mu^4}{S_\sigma^4}.$$

In one embodiment, the skewness $S_\gamma$ is defined as $$S_\gamma = \frac{S_\mu^3}{S_\sigma^3}.$$

In one embodiment, the range $S_\delta$ is defined as $S_\delta$=max $(H_k)$−min$(H_k)$.

Progression circuit 357 is configured to generate a probability that the region of tissue will experience cancer progression. Progression circuit 357 generates the probability based, at least in part, on the LoCoM signature. In one embodiment, the progression circuit 357 is configured as a machine learning classifier. In one embodiment, progression circuit 357 is configured as a quadratic discriminant analysis (QDA) machine learning classifier. In another embodiment, progression circuit 357 may be configured as a linear discriminant analysis (LDA) machine learning classifier, a support vector machine (SVM) classifier, a convolutional neural network (CNN), or a random forest (RF) classifier.

Progression circuit 357 is also configured to classify the region of tissue as a progressor or non-progressor based, at least in part, on the probability. In another embodiment, progression circuit 357 is further configured to generate a second probability that the region of tissue will experience cancer recurrence based, at least in part, on the LoCoM signature. Progression circuit 357 may, in this embodiment, be further configured to classify the region of tissue as likely to experience recurrence or unlikely to experience recurrence based, at least in part, on the second probability. In one embodiment, progression circuit 357 provides a percentage chance that the patient represented in the image will experience recurrence, or a percentage chance that the region of tissue will be a progressor or non-progressor. Progression circuit 357 classifies the region of tissue with an AUC of at least 0.72.

Progression circuit 357 resolves features extracted from the histology image at a higher order or higher level than a human can resolve in the human mind or with pencil and paper. For example, the local nuclei graphs are not biological properties of cancerous tissue that a human eye can perceive. The LoCoM signature provided to the machine learning classifier is of a different nature than the nuclei represented in the histology imagery. A region of tissue in a patient does not comprise, for example, a skewness or a kurtosis or other first order statistical feature derived from a second order statistical feature. The probability computed by progression circuit 357 and the classification is of a different nature than the underlying imagery or tissue.

In another embodiment, apparatus 300 may control a computer aided diagnosis (CADx) system to classify the region of tissue represented in the image based, at least in part, on the probability or the classification generated by progression circuit 357. For example, apparatus 300 may control a CADx system to classify a region of tissue as a progressor or non-progressor, or a patient as likely to experience recurrence or not likely to experience recurrence based, at least in part, on the probability or the classification generated by progression circuit 357. In other embodiments, other types of CADx systems may be controlled, including CADx systems for predicting recurrence or classifying a region of tissue as a progressor or non-progressor in other tissue presenting other, different pathologies that may be distinguished based on LNGs, LoCoM features or a LoCoM signature. For example, embodiments described herein may be employed to predict recurrence or cancer progression based on probabilities computed from histology imagery by a machine learning classifier in breast cancer (BCa), prostate cancer, lung cancer, kidney disease, brain pathologies, or other, cancerous pathologies.

Figure 5:
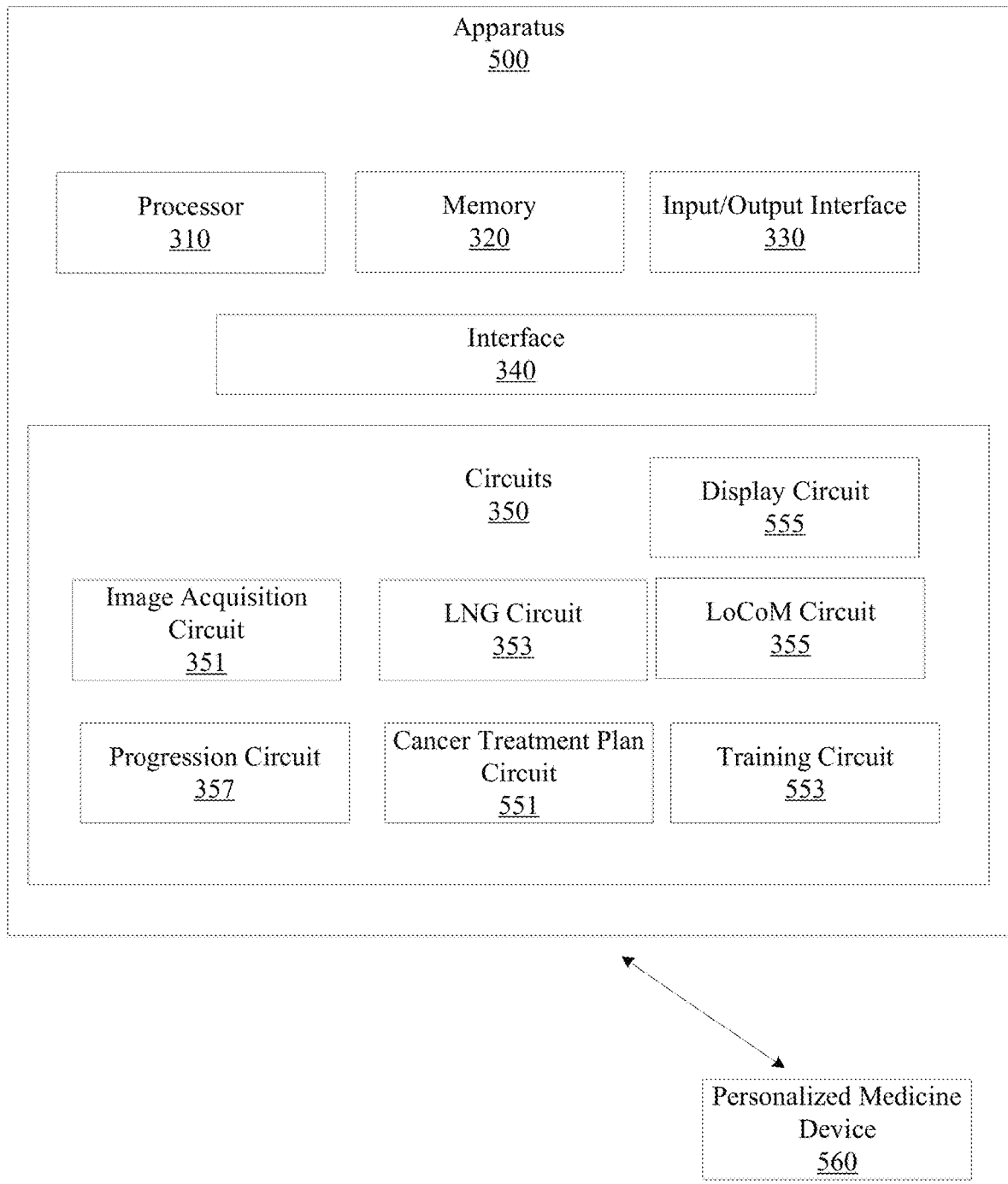
FIG. 5 illustrates an example apparatus that that predicts cancer recurrence.

FIG. 5 illustrates an apparatus 500 that is similar to apparatus 300 but that includes additional components and details. Apparatus 500 includes a cancer treatment plan circuit 551. The cancer treatment plan circuit 551 is configured to generate a cancer treatment plan based, at least in part, on the classification and at least one of the probability, the second probability, or the image. The cancer treatment plan defines an immunotherapy dosage, an immunotherapy schedule, a chemotherapy dosage, or a chemotherapy schedule for the patient represented in the image. Defining a personalized cancer treatment plan facilitates delivering a particular treatment that will be therapeutically active to the patient, while minimizing negative or adverse effects experienced by the patient. For example, the cancer treatment plan may define an immunotherapy dosage and schedule for a patient identified as a progressor while for a non-progressor, other treatments may be suggested.

In one embodiment of apparatus 500, the set of circuits 340 further includes a training circuit 553 configured to train progression circuit 357. Training progression circuit 357 may include training a machine learning classifier. In one embodiment, the training circuit 553 accesses a dataset of H&E stained TMA slides acquired from a cohort of cases of OC-SCC or OP-SCC, along with clinical follow up information, including survival data, patient age, and other clinical variables. The OC-SCC or OP-SCC cohort includes a total of 115 cases of primary OC-SCC or OP-SCC TMA slides. The H&E stained TMA is created from previously untreated patients with no history of prior cancer. For each patient, two 2 to 4 mm punches of representative blocks from their primary tumors are taken and placed on an array. Diagnoses were confirmed. In this embodiment, a single randomly selected TMA core is chosen to represent each patient, where the TMA is digitally scanned at 40× magnification using a digital scanner with a resolution of 25 μm per pixel. Patients whose disease recurred in follow up and who died with disease (e.g., patients who experienced "disease specific death") have their tissue punches on the TMA annotated on the digital images as S+. Patients whose disease did not recur or those in whom disease recurred by were successfully salvaged and were living disease free or those patients who did not die of the disease are annotated as S−. A random number generator is used to identify a set of 50 patients to include in a training set. The training set includes 17 S+ and 33 S− members. A validation set of the remaining 65 members includes 13 S+ and 52 S− members.

In this embodiment, training circuit 553 implements three different feature selection methods to select the LoCoM features that are most predictive of survival outcomes within the training set. Three feature selection approaches considered include a minimum redundancy, maximum relevance (MRMR) feature selection approach, a Wilcoxon rank sum test (WRST), and a Random Forest (RF). In this embodiment, each approach was employed in conjunction with a 5-fold cross-validation scheme and run over 50 iterations within the training set to identify the LoCoM features that maximally distinguished the two classes, while minimizing intra-feature correlation. Features are ranked by frequency of selection and the bottom 95% of features were eliminated. In another embodiment, another, different cut-off level (e.g., 90%, 99%) may be employed. Feature selection is repeated within the reduced feature family and features are again ranked by selection frequency. The top 5 most frequently selected features are identified and analyzed using box and whisker plots to compare feature expression between the S+ and S− patients within the training set. In another embodiment, other cross-validation schemes, or other numbers of iterations may be employed. For each TMA spot image, or for a threshold number of TMA spot images, each of the machine classifiers assigned a probability of recurrence. This probability is then thresholded at different points between 0 to 1, assigning each test instance to either the positive or negative categories for each threshold. The predicted labels for each classifier are then compared to the ground truth labels (true patient outcomes) to determine accuracy and AUC performance metrics. Based on the evaluation results on different classifier-feature selection scheme combinations, embodiments identify the top performing classifier-feature selection scheme combination based on the AUC values obtained on the training set. This best performing feature selection-classification combination was designated as the final pre-trained classifier, which was then independently evaluated on the validation set following which Kaplan-Meier survival analysis was performed.

Training circuit 553 may employ supervised or unsupervised learning to train progression circuit 357. In one embodiment, training circuit 553 may train progression circuit 357 until a desired level of accuracy is achieved by progression circuit 357, or until a threshold period time has been used to train progression circuit 357. In another embodiment, training circuit 553 may train progression circuit 357 until a threshold level of computational resources have be expended, until a signal instructing training circuit 553 to terminate training is received by training circuit 553, or until some other, different condition has been met.

Progression circuit 357 classifies the region of tissue with an area under the curve (AUC) of at least 0.72. In comparison, an OC-SCC or OP-SCC prediction system using a global cell graph approach achieves an AUC of 0.66+−0.04. An OC-SCC prediction system using a nuclear shape approach achieves an AUC of 0.63+−0.05. An OC-SCC prediction system using a COrE approach achieves and AUC of 0.64+−0.04. An OC-SCC prediction system using a CCG approach achieves an AUC of 0.63+−0.05. Embodiments described herein thus offer a measurable improvement over conventional systems for predicting cancer recurrence or cancer progression.

FIG. 5 further illustrates a personalized medicine device 560. Personalized medicine device 560 may be, for example, a CADx system, an OC-SCC cancer prediction system, or other type of personalized medicine device that may be used to facilitate the prediction of cancer recurrence or cancer progression. In one embodiment, the cancer treatment plan circuit 551 may control personalized medicine device 560 to display the classification, the probability, the image, a feature map, or the cancer treatment plan on a computer monitor, a smartphone display, a tablet display, or other displays.

In one embodiment of apparatus 500, the set of circuits 350 further includes a display circuit 555. The display circuit 555 may control the cancer treatment plan circuit 551 or a CADx system to display the classification, the probability, the LoCoM signature, LNGs, a feature map of nuclear morphology feature diversity, the cancer treatment plan, or the image on a computer monitor, a smartphone display, a tablet display, or other displays. Displaying the classification, the probability, the LoCoM signature, an LNG, a feature map of nuclear morphology feature diversity, the cancer treatment plan, or the image may also include printing the classification, the probability, the LoCoM signature, an LNG, a feature map of nuclear morphology feature diversity, the cancer treatment plan, or the image. The display circuit may also control the cancer treatment plan circuit 551, the progression circuit 357, or the CADx system to display operating parameters or characteristics of the machine learning classifier, during both training and testing, and during clinical operation. Displaying the classification, the probability, the LoCoM signature, an LNG, a feature map of nuclear morphology feature diversity, the cancer treatment plan, or the image involves but is not limited to extracting and changing the character of information present in a region of tissue (e.g. biological tissue), to a digitized image (e.g. digitized TMA), to changing information present in the digitized image to information of a different character in the LoCoM features, the probability, the characterization, and the cancer treatment plan. Embodiments described herein further transform the character of information to information suitable for display on, and display on, for example, a computer monitor, a smartphone display, a tablet display, or other displays. Thus, embodiments described herein use a combined order of specific rules, elements, or components that render information into a specific format that is then used and applied to create desired results more accurately and with greater reliability than conventional approaches.

FIG. 6 illustrates OP-SCC LoCoM feature map 630 and OP-SCC LoCoM feature map 635. Original H&E stained images 610 and 615 represent tissue obtained from a progressor (610) and from a non-progressor (615). The region of tissue represented in 610 is illustrated at 620 with segmented nuclei contours and connected edges overlaid as cellular sub-graphs. The region of tissue represented in 615 is illustrated at 625 with segmented nuclei contours and connected edges overlaid as cellular sub-graphs. A first LNG 621 is illustrated. LoCoM feature maps 630 and 635 illustrate cellular diversity in terms of nuclear shape for the progressor and non-progressor respectively. The different color patch 631 in LoCoM feature map 630 represents features associated with individual LNGs, in particular, first LNG 621. The different colors represented in LoCoM feature map 630 represent different low or high normalized feature values. A second LNG 626 is illustrated. The different color patch 636 in LoCoM feature map 635 represents features associated with individual LNGs, in particular, second LNG 626. Similarly, different color patches in LoCoM feature maps 630 and 635 represent other individual LNGs, and the different colors represent different low or high normalized feature values.

Figure 7:
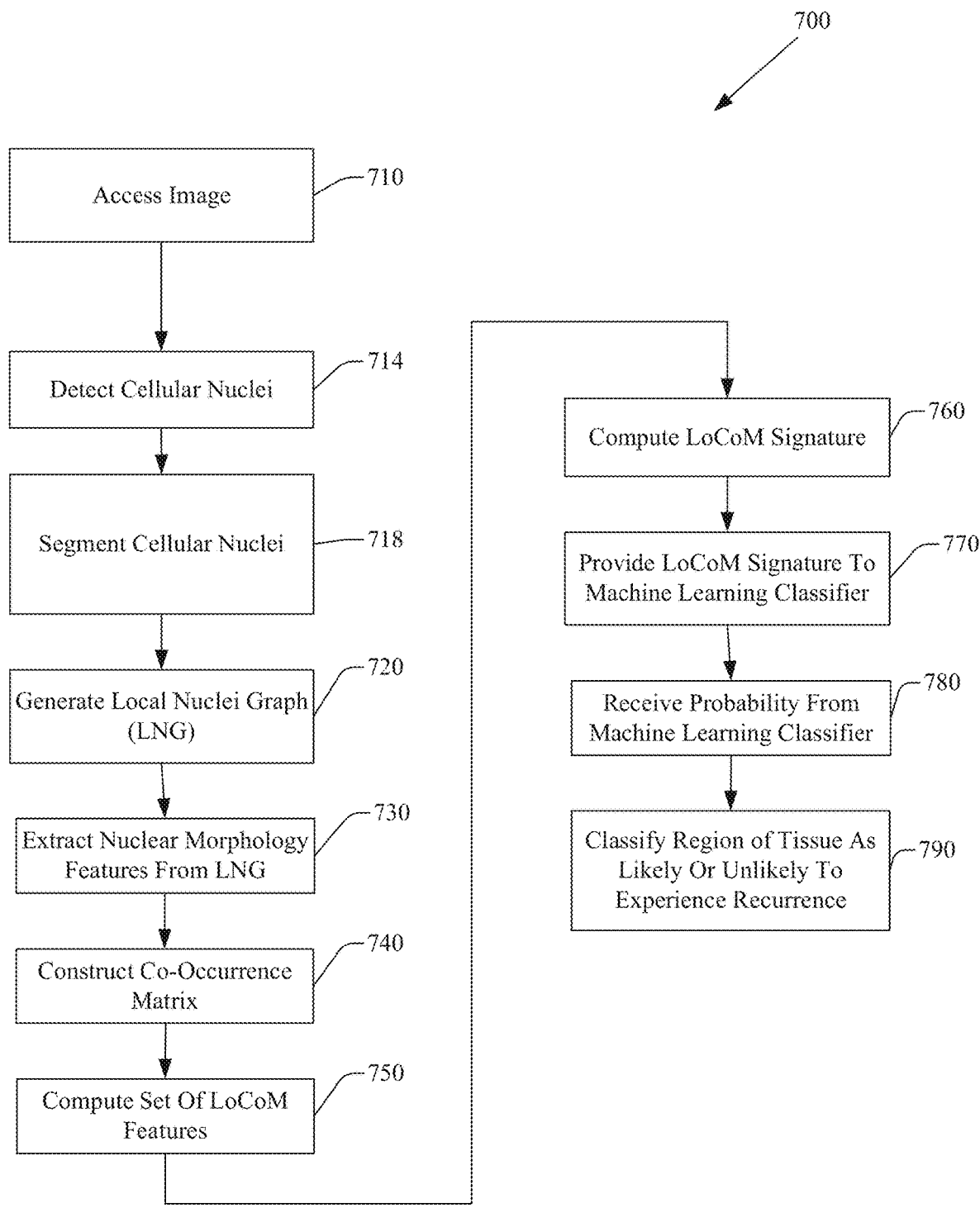
FIG. 7 illustrates an example method for predicting cancer recurrence.

FIG. 7 illustrates a computerized method 700 for predicting cancer recurrence. Method 700 includes, at 710, accessing an image of a region of tissue demonstrating cancerous pathology. The image includes a plurality of cellular nuclei. In one embodiment, accessing the image includes accessing a TMA core with a digital whole slide scanner. In different embodiments the image may be acquired from other sources that provide other fields of view, such as a digital whole slide image of a glass slide. In one embodiment, the TMA core is digitized at 40× magnification and has a resolution of 0.25 μm per pixel. In other embodiments, other magnification levels, resolutions, and imaging parameters may be employed. For example, in another embodiment, method 700 may access an H&S stained TMA core at 20× magnification, or 100× magnification. The stained TMA core may be, for example, a 0.6 mm TMA core or a 2 mm TMA core. In another embodiment, the H&E stained TMA core may be accessed at different magnification levels and have different dimensions. In other embodiments, other staining techniques or imaging modalities may be employed. Accessing the image includes acquiring electronic data, reading from a computer file, receiving a computer file, reading from a computer memory, or other computerized activity. In other embodiments, other, different types of tissue demonstrating other, different pathologies imaged using different imaging techniques may be accessed.

Method 700 also includes, at 714, detecting a member of the plurality of cellular nuclei. In one embodiment, method 700 detects a member of the plurality of cellular nuclei using multi-pass adaptive voting. In another embodiment, method 700 uses a radial symmetry transform to detect nuclei.

Method 700 also includes, at 718, segmenting the member of the plurality of cellular nuclei. In one embodiment, method 700 segments the member of the plurality of cellular nuclei using a marker-based watershed transform. In another embodiment, other automated or machine learning segmentation techniques may be employed.

Method 700 also includes, at 720, generating a local nuclei graph (LNG) based on the plurality of cellular nuclei. The LNG has at least a first node and a second node. A node in the LNG is a centroid of a member of the plurality of cellular nuclei. The probability that a first node in the LNG will be connected to a second node in the LNG is based on a probabilistic decaying function of the Euclidean distance between the first node and the second node. Multiple LNGs may be generated.

Method 700 also includes, at 730, extracting a set of nuclear morphology features from a member of the plurality of cellular nuclei associated with the node in the LNG. In one embodiment, the set of nuclear morphology features includes a shape feature and a text feature. In one embodiment, the set of nuclear morphology features includes at least seven (7) nuclear morphology features. In one embodiment, the set of nuclear morphology features includes an area feature, an eccentricity feature, a mean intensity inside the nuclei feature, an intensity range inside the nuclei feature, a mean intensity outside the nuclei, and an intensity range outside the nuclei feature. In another embodiment, another, different number of nuclear morphology features, or different nuclear morphology features, may be extracted.

Method 700 also includes, at 740, constructing a co-occurrence matrix. The co-occurrence matrix is based on the set of nuclear morphology features. In one embodiment, constructing the co-occurrence matrix includes discretizing a member of the set of nuclear morphology features along a feature dimension. Discretizing the member of the set of nuclear morphology features along the feature dimension categorizes a nucleus into a sub-class associated with the member of the set of nuclear morphology features. Multiple co-occurrence matrices may be constructed.

Method 700 also includes, at 750, computing a set of LoCoM features. The set of LoCoM features are based on the co-occurrence matrix. In one embodiment, computing the set of LoCoM features includes computing a set of Haralick features based on the co-occurrence matrix. Computing the set of LoCoM features also includes extracting a set of second-order statistical features from the set of Haralick features.

Method 700 also includes, at 760, computing a LoCoM signature based on the set of LoCoM features. Computing the LoCoM signature includes computing a set of first-order statistics from the set of second-order statistics. In one embodiment, the set of first-order statistics includes a mean, a standard deviation, a kurtosis, a skewness, and a range.

Method 700 also includes, at 770, providing the LoCoM signature to a machine learning classifier. Providing the LoCoM signature to the machine learning classifier may include acquiring electronic data, reading from a computer file, receiving a computer file, reading from a computer memory, or other computerized activity. In one embodiment, the machine learning classifier is a quadratic discriminant analysis (QDA) machine learning classifier. In another embodiment, the machine learning classifier is a support vector machine (SVM) classifier. In another embodiment, the machine learning classifier is linear discriminant analysis (LDA) machine learning classifier, a convolutional neural network (CNN), or a random forest (RF) classifier.

Method 700 also includes, at 780 receiving, from the machine learning classifier, a probability that the region of tissue will experience cancer recurrence. The machine learning classifier computes the probability based, at least in part, on the LoCoM signature. In another embodiment, method 700 also includes, at 780, receiving, from the machine learning classifier, a second probability that the region of tissue is a progressor or non-progressor. The machine learning classifier computes the probability or the second probability with an AUC of at least 0.72. Receiving the probability or second probability from the machine learning classifier may include acquiring electronic data, reading from a computer file, receiving a computer file, reading from a computer memory, or other computerized activity.

Method 700 further includes, at 790, classifying the region of tissue as likely to experience cancer recurrence or unlikely to experience cancer recurrence. Method 700 classifies the region of tissue based, at least in part, on the probability. In one embodiment, classifying the region of tissue as likely to experience cancer recurrence or unlikely to experience cancer recurrence may include classifying the region as a likely to experience recurrence when the machine learning classifier provides a probability of 0.5 or greater. In another embodiment, classifying the region of tissue may be based on other probability values (e.g., 0.6, 0.7). In one embodiment, method 700 also includes, at 790, classifying the region of tissue as a progressor or non-progressor based, at least in part, on the second probability. In another embodiment, classifying the region of tissue may include categorizing the region of tissue based on more than two categories. For example, the region of tissue may be classified as one of "likely to experience recurrence", "unlikely to experience recurrence", or "unknown" based on the probability. Other categorization schemes may be employed.

In one embodiment, method 700 further includes generating a cancer treatment plan for the patient from which the image was acquired. The cancer treatment plan is based, at least in part, on the classification and at least one of the probability, the LoCoM signature, or the image. In one embodiment, the cancer treatment plan defines an immunotherapy dosage, an immunotherapy schedule, a chemotherapy dosage, or a chemotherapy schedule. In one embodiment, method 700 further includes controlling a personalized medicine system or an OC-SCC or OP-SCC recurrence prediction system to display the cancer treatment plan. In this embodiment, method 700 may include controlling the personalized medicine system or OC-SCC or OP-SCC prediction system to display the cancer treatment plan, the classification, the probability, the LoCoM score, a color feature map, or the image.

Improved identification or classification of patients who will experience cancer recurrence or of tissue as progressor or non-progressor may produce the technical effect of improving treatment efficacy by increasing the accuracy of and decreasing the time required to treat patients demonstrating OP-SCC or other forms of cancerous pathology. Treatments and resources, including expensive immunotherapy agents, may be more accurately tailored to patients with a likelihood of benefiting from said treatments and resources, including responding to immunotherapy, so that more appropriate treatment protocols may be employed, and expensive resources are not wasted. Controlling a cancer recurrence prediction system, a CADx system, or a personalized medicine system based on improved identification or classification of patients who will experience recurrence or progression further improves the operation of the system, since unnecessary operations will not be performed.

Using a more appropriately modulated treatment may lead to less aggressive therapeutics being required for a patient or may lead to avoiding or delaying a biopsy, a resection, or other invasive procedure. When patients experiencing OP-SCC or other forms of cancerous pathology who will experience recurrence or progression are more quickly and more accurately distinguished from patients who will not, patients most at risk may receive a higher proportion of scarce resources (e.g., therapeutics, physician time and attention, hospital beds) while those less likely to benefit from the treatment may be spared unnecessary treatment, which in turn spares unnecessary expenditures and resource consumption. Example methods, apparatus, and other embodiments may thus have the additional effect of improving patient outcomes compared to conventional approaches.

While FIG. 7 illustrates various actions occurring in serial, it is to be appreciated that various actions illustrated in FIG. 7 could occur substantially in parallel. By way of illustration, a first process could involve detecting cellular nuclei, a second process could involve constructing LNGs, and a third process could involve computing a LoCoM signature. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods described or claimed herein including method 700. While executable instructions associated with the listed methods are described as being stored on a computer-readable storage device, it is to be appreciated that executable instructions associated with other example methods described or claimed herein may also be stored on a computer-readable storage device. In different embodiments the example methods described herein may be triggered in different ways. In one embodiment, a method may be triggered manually by a user. In another example, a method may be triggered automatically.

Figure 8:
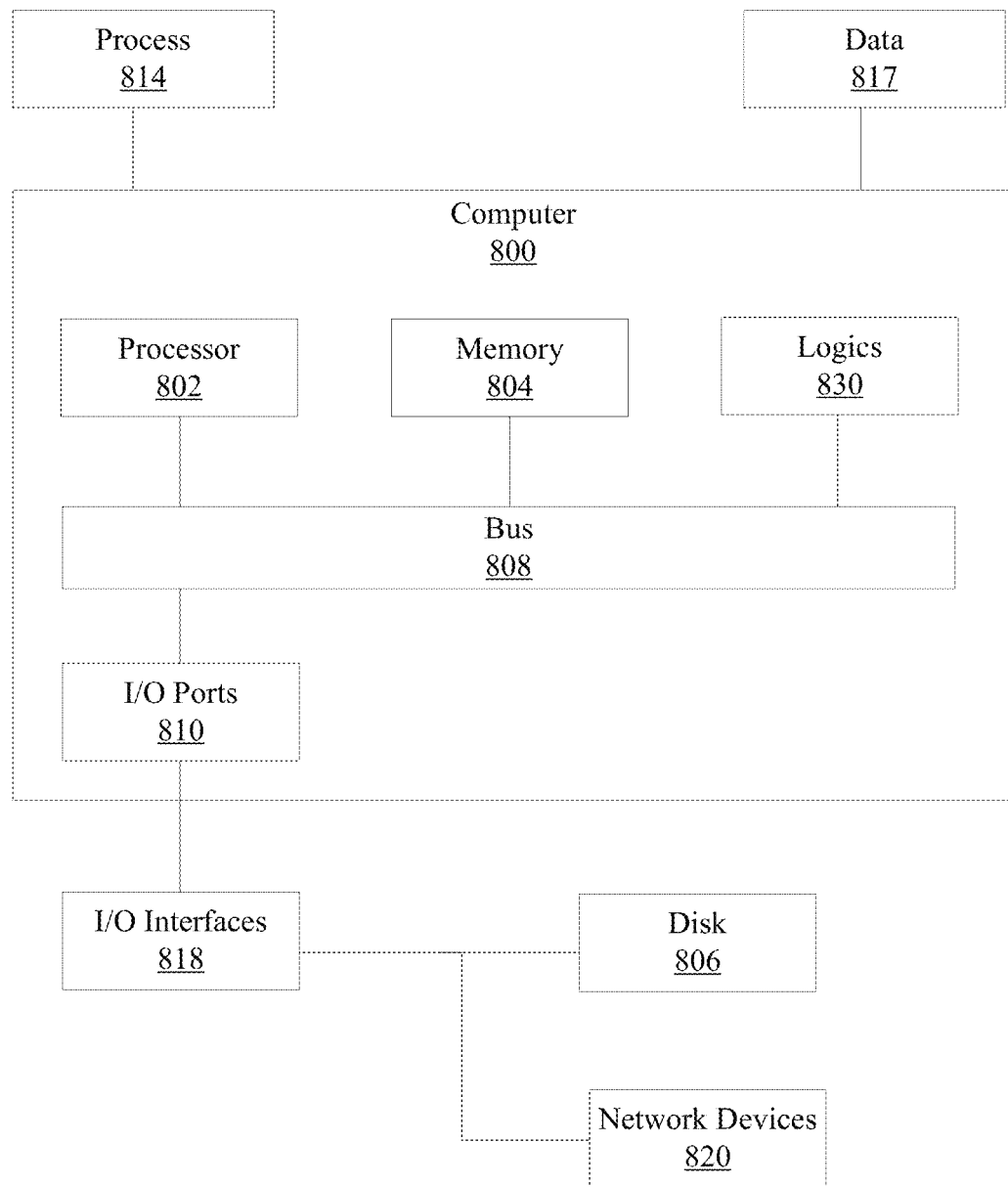
FIG. 8 illustrates an example computer in which example embodiments described herein may operate.

FIG. 8 illustrates an example computer 800 in which example methods illustrated herein can operate and in which example methods, apparatus, circuits, operations, or logics may be implemented. In different examples, computer 800 may be part of a personalized medicine system, a cancer recurrence prediction system, a cancer progression prediction system, a digital whole slide scanner, a CT system, may be operably connectable to a digital whole slide scanner, a CT system, an MRI system, a personalized medicine system, or may be part of a CADx system.

Computer 800 includes a processor 802, a memory 804, and input/output (I/O) ports 810 operably connected by a bus 808. In one example, computer 800 may include a set of logics or circuits 830 that perform a method of predicting cancer recurrence or cancer progression using a machine learning classifier. Thus, the set of logics or circuits 830, whether implemented in computer 800 as hardware, firmware, software, and/or a combination thereof may provide means (e.g., hardware, firmware, circuits) for predicting cancer recurrence or cancer progression based on a LoCoM signature and a machine learning classifier. In different examples, the set of circuits 830 may be permanently and/or removably attached to computer 800.

Processor 802 can be a variety of various processors including dual microprocessor and other multi-processor architectures. Processor 802 may be configured to perform steps of methods claimed and described herein. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a flash memory card, or a memory stick. Furthermore, disk 806 may include optical drives like a CD-ROM or a digital video ROM drive (DVD ROM). Memory 804 can store processes 814 or data 817, for example. Data 817 may, in one embodiment, include digitized CT images of a region of tissue demonstrating NSCLC. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, circuits, logics, and peripherals using other buses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, CT systems, MRI systems, digital whole slide scanners, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks, including the cloud.

Examples herein can include subject matter such as an apparatus, a personalized medicine system, a CADx system, a processor, a system, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting cancer recurrence or cancer progression according to embodiments and examples described.

One example embodiment includes a computer-readable storage device storing computer-executable instructions that, in response to execution, cause a cancer recurrence prediction system, a cancer progression prediction system, or a processor, to perform operations. The operations may include accessing an image of a region of tissue demonstrating cancerous pathology that includes a plurality of cellular nuclei. In one embodiment the image is an H&E stained tissue microarray (TMA) core of a region of tissue demonstrating oral cavity squamous cell cancer (OCSCC) digitized at 40× magnification and 0.25 μm per pixel resolution.

A cancer recurrence prediction system, a cancer progression prediction system, or processor may include circuitry such as, but not limited to, one or more single-core or multi-core processors. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The operations may also include detecting a member of the plurality of cellular nuclei using multipass adaptive voting. The operations may also include detecting a member of the plurality of cellular nuclei using other nuclei detection techniques.

The operations may also include segmenting the member of the plurality of cellular nuclei using a marker-based watershed transform. The operations may also include segmenting the member of the plurality of cellular nuclei using other segmentation techniques.

The operations may also include generating a local nuclei graph (LNG) based on the plurality of cellular nuclei. The LNG has at least a first node and a second node. A node in the LNG is a centroid of a member of the plurality of cellular nuclei. The probability that a first node in the LNG will be connected to a second node in the LNG is based on a probabilistic decaying function of the Euclidean distance between the first node and the second node. Multiple LNGs may be generated.

The operations may also include extracting a set of nuclear morphology features from a member of the plurality of cellular nuclei associated with the node in the LNG. The set of nuclear morphology features includes a texture feature and a shape feature.

The operations may also include constructing a co-occurrence matrix based on the set of nuclear morphology features. Multiple co-occurrence matrices may be constructed.

The operations may also include generating a set of LoCoM features based on the co-occurrence matrix by computing a set of Haralick features based on the co-occurrence matrix. The operations further include extracting a set of second-order statistical features from the set of Haralick features.

The operations may also include computing a LoCoM signature based on the set of LoCoM features. The operations include computing a set of first-order statistics from the set of second-order statistics.

The operations may also include providing the LoCoM signature to a quadratic discriminant analysis (QDA) machine learning classifier.

The operations may also include receiving, from the machine learning classifier, a probability that the region of tissue will experience cancer recurrence or that the region of tissue will experience cancer progression. The machine learning classifier computes the probability based, at least in part, on the LoCoM signature.

The operations may further include classifying the region of tissue as likely to experience cancer recurrence or unlikely to experience cancer recurrence, or as a progressor or non-progressor. The operations base the classification, at least in part, on the probability.

The operations also include computing a probability that the region of tissue will experience cancer recurrence or that the region of tissue will experience cancer progression, based, at least in part, on the LoCoM signature. Computing the probability may include, in one embodiment, providing the LoCoM signature or the set of LoCoM features to a machine learning classifier. The machine learning classifier may be an SVM, a QDA classifier, an LDA classifier, a random forests classifier, a CNN, or other type of machine learning classifier. In this embodiment, the machine learning classifier computes a probability that the region of tissue will experience cancer recurrence or that the region of tissue will experience cancer progression, based, at least in part, on the LoCoM signature. In one embodiment, the operations further include training the machine learning classifier. In one embodiment, the operations further include testing the machine learning classifier on a held-out testing dataset.

The operations also include classifying the region of tissue as likely to experience cancer recurrence or unlikely to experience cancer recurrence, or as a progressor or non-progressor. The classification is based, at least in part, on the probability. In one embodiment, the region of tissue is classified as a progressor or non-progressor when the probability has a value of 0.5 or greater. In another embodiment, the region of tissue is classified as a progressor or non-progressor when the probability has another, different value. In one embodiment, the region of tissue is classified as likely to experience recurrence when the probability has a value of 0.5 or greater. In another embodiment, the region of tissue is classified as likely to experience recurrence when the probability has another, different value. In one embodiment, the region of tissue is classified with an AUC of at least 0.72.

In one embodiment, the operations further include generating a cancer treatment plan. The cancer treatment plan is based, at least in part, on the classification and at least one of the probability, the LoCoM signature, or the set of LoCoM features.

In one embodiment, the operations further include controlling a personalized medicine system, a CADx system, or processor to display the probability, the LoCoM signature, the set of LoCoM features, a feature map based on the set of LoCoM features, or the cancer treatment plan, on a computer monitor, a smartphone display, a tablet display, or other displays.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An apparatus for predicting recurrence of cancer, the apparatus comprising:
   a processor;
   a memory that stores a digitized image of a region of tissue demonstrating cancerous pathology, where the image includes at least one cellular nucleus, where the image includes a pixel, the pixel having an intensity;
   an input/output (I/O) interface;
   a set of circuits comprising an image acquisition circuit, a local nuclei graph (LNG) circuit, a local co-occurrence of cell morphology (LoCoM) circuit, and a progression circuit; and
   an interface to connect the processor, the memory, the I/O interface and the set of circuits;
   the image acquisition circuit configured to:
      access the image of a region of tissue demonstrating cancerous pathology;
      identify at least one cellular nucleus represented in the image, where the at least one cellular nucleus has a centroid; and
      segment the at least one cellular nucleus;
   the LNG circuit configured to:
      construct an LNG based on the at least one cellular nucleus identified by the image acquisition circuit, where a vertex in the LNG is a cellular nucleus centroid; and
      compute a set of nuclear morphology features for a nucleus represented in the LNG, where the set of nuclear morphology features includes an area feature, an eccentricity feature, an orientation feature, a mean intensity inside the nuclei feature, an intensity range inside the nuclei feature, a mean intensity outside the nuclei feature, and an intensity range outside the nuclei feature;
   the LoCoM circuit configured to:
      construct a co-occurrence matrix based on the set of nuclear morphology features;
      compute a set of LoCoM features for the co-occurrence matrix; and
      compute a LoCoM signature for the image based on the set of LoCoM features;

the progression circuit configured to:
  generate a probability that the region of tissue will experience cancer progression based, at least in part, on the LoCoM signature; and
  classify the region of tissue as a progressor or non-progressor based, at least in part, on the probability.

2. The apparatus of claim 1, where accessing the image includes accessing a hematoxylin and eosin (H&E) stained tissue microarray (TMA) core of a region of tissue demonstrating oral cavity squamous cell cancer (OCSCC) with a digital whole-slide scanner.

3. The apparatus of claim 2, where the TMA core is digitized at 40× magnification and 0.25 µm per pixel resolution.

4. The apparatus of claim 1, where the image acquisition circuit is configured to identify a cellular nucleus represented in the image using multi-pass adaptive voting.

5. The apparatus of claim 1, where the image acquisition circuit is configured to segment the cellular nucleus using a marker-based watershed transform.

6. The apparatus of claim 1, where the probability that a first vertex in the LNG will be connected to a second vertex in the LNG is based on a probabilistic decaying function of the Euclidean distance between the first vertex and the second vertex.

7. The apparatus of claim 1, where constructing the co-occurrence matrix based on the set of nuclear morphology features includes discretizing a member of the set of nuclear morphology features along a feature dimension, where discretizing the member of the set of nuclear morphology features along the feature dimension categorizes a nucleus into a sub-class associated with the member of the set of nuclear morphology features.

8. The apparatus of claim 1, where computing the set of LoCoM features comprises computing a set of Haralick features based on the co-occurrence matrix, and extracting a set of second-order statistical features from the set of Haralick features.

9. The apparatus of claim 8, where computing the LoCoM signature includes computing a set of first-order statistics from the set of second-order statistics.

10. The apparatus of claim 9, where the set of first-order statistics includes a mean, a standard deviation, a kurtosis, a skewness, and a range.

11. The apparatus of claim 1, where the progression circuit is configured as a quadratic discriminant analysis (QDA) machine learning classifier, a linear discriminant analysis (LDA) machine learning classifier, a support vector machine (SVM) classifier, a convolutional neural network (CNN), or a random forest (RF) classifier, and where the progression circuit classifies the region of tissue with an accuracy of at least 0.72 area under the curve (AUC).

12. The apparatus of claim 1, where the progression circuit is further configured to:
  generate a second probability that the region of tissue will experience cancer recurrence based, at least in part, on the LoCoM signature; and
  classify the region of tissue as likely to experience recurrence or unlikely to experience recurrence based, at least in part, on the second probability.

13. The apparatus of claim 12, the set of circuits further comprising a cancer treatment plan circuit configured to generate a cancer treatment plan based, at least in part, on the classification and at least one of the probability, the second probability, or the image, where the cancer treatment plan defines an immunotherapy dosage, an immunotherapy schedule, a chemotherapy dosage, or a chemotherapy schedule.

14. A non-transitory computer-readable storage device storing computer-executable instructions that when executed by a computer control the computer to perform a method for predicting cancer recurrence, the method comprising:
  accessing an image of a region of tissue demonstrating cancerous pathology, where the image includes a plurality of cellular nuclei;
  detecting a member of the plurality of cellular nuclei;
  segmenting the member of the plurality of cellular nuclei;
  generating a local nuclei graph (LNG) based on the plurality of cellular nuclei, the LNG having at least a first node and a second node, where a node in the LNG is a centroid of a member of the plurality of cellular nuclei, where the probability that the first node in the LNG will be connected to the second node in the LNG is based on a probabilistic decaying function of the Euclidean distance between the first node and the second node;
  extracting a set of nuclear morphology features from a member of the plurality of cellular nuclei associated with the node in the LNG, where the set of nuclear morphology features includes an area feature, an eccentricity feature, an orientation feature, a mean intensity inside the nuclei feature, an intensity range inside the nuclei feature, a mean intensity outside the nuclei feature, and an intensity range outside the nuclei feature;
  constructing a co-occurrence matrix based on the set of nuclear morphology features;
  computing a set of local co-occurrence of cell morphology (LoCoMI features based on the co-occurrence matrix;
  computing a LoCoM signature based on the set of LoCoM features;
  providing the LoCoM signature to a machine learning classifier;
  receiving, from the machine learning classifier, a probability that the region of tissue will experience cancer recurrence, where the machine learning classifier computes the probability based, at least in part, on the LoCoM signature; and
  classifying the region of tissue as likely to experience cancer recurrence or unlikely to experience cancer recurrence based, at least in part, on the probability.

15. The non-transitory computer-readable storage device of claim 14, where constructing the co-occurrence matrix includes discretizing a member of the set of nuclear morphology features along a feature dimension, where discretizing the member of the set of nuclear morphology features along the feature dimension categorizes a nucleus into a sub-class associated with the member of the set of nuclear morphology features.

16. The non-transitory computer-readable storage device of claim 15, where computing the set of LoCoM features comprises computing a set of Haralick features based on the co-occurrence matrix, and extracting a set of second-order statistical features from the set of Haralick features, and where computing the LoCoM signature includes computing a set of first-order statistics from the set of second-order statistics.

17. The non-transitory computer-readable storage device of claim 14, where the machine learning classifier is a quadratic discriminant analysis (QDA) machine learning classifier, a linear discriminant analysis (LDA) machine learning classifier, a support vector machine (SVM) classifier, a convolutional neural network (CNN), or a random forest (RF) classifier, and where the machine learning classifier computes the probability with an area under the curve (AUC) of at least 0.72.

18. A computer-readable storage device storing computer-executable instructions that, in response to execution, cause a cancer recurrence prediction system to perform operations comprising:

accessing an image of a region of tissue demonstrating cancerous pathology, where the image includes a plurality of cellular nuclei, where the image is a hematoxylin and eosin (H&E) stained tissue microarray (TMA) core of a region of tissue demonstrating oral cavity squamous cell cancer (OCSCC) digitized at 40× magnification and 0.25 µm per pixel resolution;

detecting a member of the plurality of cellular nuclei using multipass adaptive voting;

segmenting the member of the plurality of cellular nuclei using a marker-based watershed transform;

generating a local nuclei graph (LNG) based on the plurality of cellular nuclei, the LNG having at least a first node and a second node, where a node in the LNG is a centroid of a member of the plurality of cellular nuclei, where the probability that a first node in the LNG will be connected to a second node in the LNG is based on a probabilistic decaying function of the Euclidean distance between the first node and the second node;

extracting a set of nuclear morphology features from a member of the plurality of cellular nuclei associated with the node in the LNG, where the set of nuclear morphology features includes a texture feature and a shape feature;

constructing a co-occurrence matrix based on the set of nuclear morphology features;

generating a set of local co-occurrence of cell morphology (LoCoM) features based on the co-occurrence matrix by computing a set of Haralick features based on the co-occurrence matrix, and extracting a set of second-order statistical features from the set of Haralick features;

computing a LoCoM signature based on the set of LoCoM features by computing a set of first-order statistics from the set of second-order statistics;

computing a probability that the region of tissue will experience cancer recurrence or that the region of tissue will experience cancer progression, based, at least in part, on the LoCoM signature; and classifying the region of tissue as likely to experience cancer recurrence or unlikely to experience cancer recurrence, or as a progressor or non-progressor, based, at least in part, on the probability.

19. The non-transitory computer-readable storage device of claim 14, where the cancerous pathology that the image of the region of tissue demonstrates is oral cavity squamous cell cancer (OCSCC).

20. The non-transitory computer-readable storage device of claim 14, where segmenting the member of the plurality of cellular nuclei comprises using a marker-based watershed transform.

* * * * *

UNITED STATES PATENT AND TRADEMARK OFFICE
CERTIFICATE OF CORRECTION

PATENT NO. : 10,783,627 B2
APPLICATION NO. : 15/898728
DATED : September 22, 2020
INVENTOR(S) : Anant Madabhushi et al.

Page 1 of 1

It is certified that error appears in the above-identified patent and that said Letters Patent is hereby corrected as shown below:

In the Specification

Column 1, Lines 13 through 26; please replace "This invention was made with government support under the National Cancer Institute of the National Institutes of Health award numbers 1U24CA199374-01, R01CA202752-01A1, R01CA208236-01A1, R21CA195152-01, R21CA179327-01A1, the National Institute of Diabetes and Digestive and Kidney Diseases under award number R01DK098503-02, National Center for Research Resources under award number 1 C06 RR12463-01, the DOD Prostate Cancer Synergistic Idea Development Award (PC120857), the DOD Lung Cancer Idea Development New Investigator Award (LC130463), the DOD Prostate Cancer Idea Development Award, and the DOD Peer Reviewed Cancer Research Program W81XWH-16-1-0329. The government has certain rights in the invention." with --This invention was made with government support under grant(s) CA179327, CA195152, DK098503, CA199374, CA202752, CA208236, RR012463 awarded by the National Institutes of Health; and grant(s) W81XWH-16-1-0329, W81XWH-14-1-0323, W81XWH-13-1-0418, and W81XWH-15-1-0558 awarded by the Department of Defense. The government has certain rights in the invention.--

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*